United States Patent [19]

Sanders

[11] Patent Number: 4,820,866

[45] Date of Patent: Apr. 11, 1989

[54] PROCESS FOR THE PRODUCTION OF DIISOCYANATES, SELECTED DIISOCYANATES PRODUCED THEREBY AND THE PRODUCTION OF POLYURETHANE PLASTICS THEREFROM

[75] Inventor: Josef Sanders, Koeln, Fed. Rep. of Germany

[73] Assignee: Bayer Aktiengesellschaft, Bayerwerk, Fed. Rep. of Germany

[21] Appl. No.: 84,547

[22] Filed: Aug. 12, 1987

[30] Foreign Application Priority Data

Aug. 21, 1986 [DE] Fed. Rep. of Germany ....... 3628316

[51] Int. Cl.$^4$ .............................................. C07C 69/00
[52] U.S. Cl. ..................................... 560/347; 560/358
[58] Field of Search ................................ 560/347, 358

[56] References Cited

U.S. PATENT DOCUMENTS 4,328,166 5/1982 Fujita et al. .......................... 260/453
4,597,910 7/1986 Konig et al. ......................... 560/359

FOREIGN PATENT DOCUMENTS 1539183 1/1979 United Kingdom .

OTHER PUBLICATIONS

Chemical Abstracts, Jan. 10, 1955, No. 1, vol. 49, F. H. McMillan, "Diaryloxyalkane Derivates".
Chemistry of Ether Linkage, S. Patai, 1967, pp. 450 et seq., Interscience Publishers.
Houben Weyl, vol. VI/3, p. 77.

Primary Examiner—Alan Siegel
Attorney, Agent, or Firm—Gene Harsh; Joseph C. Gil; Richard E. L. Henderson

[57] ABSTRACT

Diisocyanates corresponding to a specified formula are produced by reacting an alcohol corresponding to a specified formula with a nitrochlorobenzene in the presence of NaOH and/or KOH in powder form and a strongly polar, aprotic solvent to produce a dinitro compound corresponding to a specified formula. This dinitro compound is hydrogenated to form the corresponding diamine which diamine is phosgenated to produce the corresponding diisocyanate. The resultant diisocyanates may then be used as starting materials in polyisocyanate addition processes.

4 Claims, No Drawings

PROCESS FOR THE PRODUCTION OF DIISOCYANATES, SELECTED DIISOCYANATES PRODUCED THEREBY AND THE PRODUCTION OF POLYURETHANE PLASTICS THEREFROM

BACKGROUND OF THE INVENTION

This invention relates to a new process for the production of diisocyanates having a bis-(isocyanatophenoxy)-alkane structure, to new diisocyanates obtainable by this process and to their use as a synthesis component in the production of polyurethane plastics by the isocyanate polyaddition process.

DE-OS No. 3,442,689 describes certain bis-(4-isocyanatophenoxy)-alkanes which are comparable to 1,5-diisocyanatonaphthalene in their suitability for the production of high-quality polyurethane elastomers. Only those diisocyanates which contain unbranched alkylene radicals between the two ether oxygen atoms are specifically described. However, these known diisocyanates have certain disadvantages both in regard to their properties and in regard to their producibility, i.e. in regard to the producibility of the intermediates on which they are based. Their melting points (88°-98° C.) are relatively high and their solubility in apolar organic solvents is unsatisfactory. As a result, they are often difficult and comparatively expensive to process in the melt and in solution. The production of the dinitro compounds on which they are based by conventional methods is also uneconomical. The condensation of alkali-4-nitrophenolate with alkane dihalides only gives acceptable yields where expensive alkane dibromides are used. In addition, part of these expensive dibromides is irreversibly consumed in a secondary reaction with elimination of hydrogen bromide. This secondary reaction can become the main reaction where branched alkane dihalides are used. Sterically hindered alkane dihalides such as 1,3-dihalogen-2,2-dialkylpropanes cannot be reacted at all to form the corresponding bis-(nitrophenoxy)-alkanes by these processes.

Although DE-OS No. 3,442,689 mentions the reaction of 4-nitrochlorobenzene with alkane diols or with (4-nitrophenoxy)-alkanols in the presence of bases as another method for producing the dinitro compounds, there is no reference whatever to the type of base to be used or to any solvents which may be present. The obvious choice of an aqueous sodium hydroxide as base leads to unsatisfactory yields of the corresponding dinitro compounds, even in cases where inert solvents, such as chlorobenzene, are used. In addition, a procedure such as this is totally unsuitable for the production of dinitro compounds containing a branched alkane radical. Use of alkali metals as "base" does not produce the desired result either, because secondary reactions occur to a considerable extent even in cases where monohydric alcohols are used (c.f. The Chemistry of the Ether Linkage, Ed. S. Patai, Interscience Publishers, 1967, p. 450; Houben Weyl, Vol. VI/3, p.77).

The phase-transfer-catalyzed reaction of nitrochlorobenzenes with organic hydroxy compounds in aqueous-/organic two-phase systems described in DE-OS No. 2,634,419 also leads to only traces of the desired bis-nitrophenoxyalkanes where 2- or 4-nitrochlorobenzene is used. Instead, the main products obtained are dichloroazoxybenzenes and the corresponding nitrophenoxyalkanols.

SUMMARY OF THE INVENTION

It is an object of the present invention to provide a new process for the production of diisocyanates having a bis-(isocyanatophenoxy)-alkane structure from (i) alkanediols or nitrophenoxyalkanols and (ii) optionally methyl-substituted nitrochlorobenzenes which is not attended by any of the above-mentioned disadvantages of the known processes and which also enables bis-(isocyanatophenoxy)-alkanes containing branched alkane radicals to be produced for the first time.

It is also an object of the present invention to provide bis-(isocyanatophenoxy)-alkanes containing branched alkane radicals.

These and other objects which will be apparent to those skilled in the art are accomplished by reacting an alcohol corresponding to a specified formula with a nitrochlorobenzene in the presence of NaOH and/or KOH powder and a strongly polar, aprotic solvent to produce a dinitro compound corresponding to a specified formula. This dinitro compound is hydrogenated to form the corresponding diamine which diamine is phosgenated to produce the corresponding diisocyanate. The resultant diisocyanates may then be used as starting materials in polyisocyanate addition processes.

DETAILED DESCRIPTION OF THE INVENTION

An important feature of the present invention is the fact that the dinitro compounds on which the diisocyanates are based can be produced in high yields by reaction of nitrochlorobenzenes with alkanediols or with nitrophenoxyalkanes in the presence of bases when powdered sodium and/or potassium hydroxide are used as bases and when, at the same time, the reaction is carried out in the presence of certain quantities of strongly polar aprotic solvents. The process of the present invention is not only suitable for the production of known diisocyanates of the type described, for example, in DE-OS No. 3,442,689, it may also be used for the production of hitherto unknown diisocyanates having a bis-(isocyanatophenoxy)-alkane structure containing branched alkylene radicals which are distinguished with advantage from the diisocyanates according to DE-OS No. 3,442,689 by the fact that they have a lower melting point or are liquid at room temperature.

The present invention relates to a process for the production of diisocyanates corresponding to the general formula

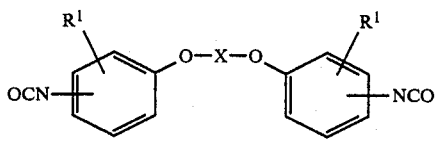

by
(a) reaction of
(i) monofunctional or difunctional alcohols corresponding to the formula

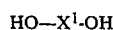

or the formula

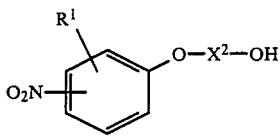

with (ii) compounds corresponding to the following general formula

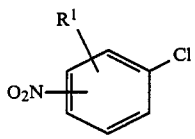

to form the corresponding dinitro compounds represented by the following general formula

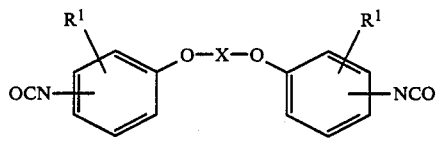

in which in each of the above formulae, $R^1$ represents hydrogen or a methyl group, $X^1$ represents a difunctional aliphatic hydrocarbon radical containing from 2 to 31 carbon atoms, with the proviso that at least two carbon atoms are arranged between the two hydroxyl groups, $X^2$ represents a difunctional, aliphatic hydrocarbon radical optionally interrupted by ether bridges and containing from 2 to 9 carbon atoms, with the proviso that at least two carbon atoms are arranged between the two free valencies and X has the same meaning as $X^1$ or $X^2$ (b) hydrogenation of the dinitro compounds thus obtained by a known method to form the corresponding diprimary diamines and (c) phosgenation of the diamino compounds obtained in b) by known methods.

The reaction (a) is carried out in the presence of powdered sodium and/or potassium hydroxide in a quantity at least sufficient to neutralize the hydrogen chloride eliminated and in the presence of a strongly polar aprotic solvent.

The present invention also relates to diisocyanates corresponding to the general formula

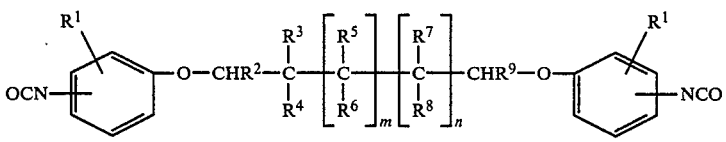

in which $R^1$ represents hydrogen or a methyl group and $R^2$, $R^3$, $R^5$, $R^6$, $R^7$, $R^8$ and $R^9$ represent hydrogen or $C_1$–$C_4$ alkyl radicals, $R^4$ represents a $C_1$–$C_4$ alkyl radical and m and n=0 or 1.

The present invention also relates to the use of the diisocyanates of the present invention as a synthesis component in the production of polyurethane plastics by the isocyanate polyaddition process.

Starting materials for the process according to the invention are (i) monofunctional or difunctional alcohols and (ii) nitrochlorobenzenes which are optionally methyl-substituted.

Suitable alcoholic synthesis components (i) are diols corresponding to the general formula $HO-X^1-OH$ in which $X^1$ is as already defined and preferably represents a linear or branched, most preferably branched, alkylene radical containing from 2 to 8 carbon atoms. Suitable alkanediols include linear diols such as ethylene glycol, 1,3-dihydroxypropane, 1,4-dihydroxybutane, 1,5-dihydroxypentane, 1,6-dihydroxyhexane, 1,8-dihydroxyoctane; branched diols such as 2-methyl-1,3-dihydroxypropane, 3-methyl-1,5-dihydroxypentane and 2-ethyl-1,3-dihydroxyhexane; alkanediols containing cycloaliphatic rings such as 1,4-bis-(hydroxymethyl)-cyclohexane (The term "alkanediol" is also intended to encompass aliphatic-cycloaliphatic diols such as these); and diols containing the structural unit

in which $R^3$ is hydrogen or a $C_1$–$C_4$ alkyl radical, preferably a methyl group, and $R^4$ represents a $C_1$–$C_4$ alkyl radical, preferably a methyl group, in particular diols corresponding to the general formula

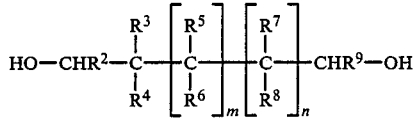

in which $R^2$, $R^3$, $R^5$, $R^6$, $R^7$, $R^8$ and $R^9$ represent hydrogen or $C_1$–$C_4$ alkyl radicals, $R^4$ represents a $C_1$–$C_4$ alkyl radical and m and n—0 or 1.

Particularly preferred alkanediols include those corresponding to the general formula immediately above in which $R^2$, $R^5$, $R^6$, $R^7$ and $R^9$ represent hydrogen, $R^3$ and $R^4$ are methyl groups, $R^8$ is hydrogen or a methyl group and m and n are as defined above.

The most preferred alkanediols include 2,2-dimethyl-1,3-dihydroxypropane, 2-methyl-2-propyl-1,3-dihydroxypropane, 2,2-diethyl-1,3-dihydroxypropane, 2,2,4-trimethyl-1,3-dihydroxypentane and 2,2,4-trimethyl-1,6-dihydroxyhexane.

Other alcoholic starting materials (i) include monofunctional alcohols corresponding to the general formula

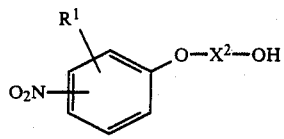

in which $R^1$ and $X^2$ are as already defined, $R^1$ preferably being hydrogen and $X^2$ preferably being a radical corresponding to the general formula

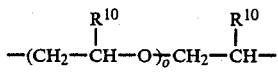

in which $R^{10}$ is hydrogen or a methyl group and $o=0$ or 1, the hydroxyl group being attached to the secondary carbon atom. In these compounds, the nitro group is preferably in the ortho or para position to the oxygen atom attached to the benzene ring.

Examples of monohydric alcohols such as these are 1-(2-hydroxyethoxy)-2-nitrobenzene, 1-(2-hydroxyethoxy)-4-nitrobenzene, 1-(2-hydroxypropoxy)-2-nitrobenzene, 1-(2-hydroxypropoxy)-4-nitrobenzene and the alkoxylation products of these compounds containing more than one ether group and corresponding to the above criteria.

The nitrochlorobenzene starting materials (ii) suitable for use in accordance with the invention include optionally methyl-substituted nitrochlorobenzenes corresponding to the general formula

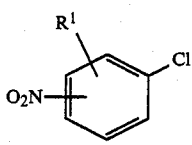

in which $R^1$ represents hydrogen or a methyl group, preferably hydrogen, and in which the chlorine and nitro substituents are preferably in the ortho position or para position to one another. Suitable nitrochlorobenzenes such as these are, for example, 2-nitrochlorobenzene, 4-nitro-chlorobenzene, 1-methyl-2-nitro-3-chlorobenzene, 1-methyl-4-nitro-5-chlorobenzene or 1-methyl-2-nitro-6-chlorobenzene. Particularly preferred starting materials (ii) are 2-nitrochlorobenzene or 4-nitro-chlorobenzene.

In stage a) of the process of the present invention, the nitrochlorobenzene starting materials (ii) may be used in stoichiometric quantities, in more than stoichiometric and in less than stoichiometric quantities, based on alcohol component (i). The nitrochlorobenzene component (ii) is preferably used in a quantity such that there are from 1 to 1.5 mols of component (ii) for every mol of hydroxyl groups of component (i).

Stage (a) of the process of the present invention is carried out in the presence of powdered alkali hydroxide, i.e. powdered sodium and/or potassium hydroxide, preferably powdered sodium hydroxide. The mean particle size of the powdered alkali hydroxides is generally from 1 to 25 m. Powdered sodium hydroxides such as these are commercially available, for example, from Reininghauss-Chemie, D-4300 Essen.

The alkali hydroxides are preferably used in a quantity at least sufficient to neutralize the hydrogen chloride eliminated. It is particularly preferred to use the alkali hydroxides in a quantity such that from 1.3 to 2 mols of alkali hydroxide are available for every mol of hydroxyl groups of component (i).

Stage (a) of the process of the present invention is carried out in the presence of polar aprotic solvents. These solvents are preferably those which have a dipole moment of at least 2.0 and more preferably of at least 3.0 Debye. Examples of solvents such as these are acetone, acetonitrile, dimethylformamide, dimethylacetamide, dimethylsulfoxide, tetramethylene sulfone, furfurol, nitromethane, nitropropane, nitrobenzene, N-methylpyrrolidone, hexamethylene phosphoric acid triamide, tetramethyl urea, trimethyl urea, ethylene glycol diethyl ether and mixtures of these solvents. Dimethylsulfoxide and dimethylformamide are preferably used. The quantity in which the solvent is used is generally gauged in such a way that it is sufficient to dissolve the starting materials (i) and (ii) and to ensure that, on completion of the condensation reaction, the mostly solid dinitro compounds are largely precipitated on cooling of the reaction mixture to room temperature and may be isolated by simple filtration. Although larger quantities of solvent may be used, they are uneconomical. In practice, this means that the solvents are generally used in a quantity of from 100 to 300 parts by weight solvent to 100 parts by weight of the mixture of components (i) and (ii).

Stage (a) of the process of the present invention may be carried out, for example, by initially introducing the starting materials (i) and (ii) in the solvent selected and adding the solid, powder-form alkali hydroxide either in portions or continuously with stirring and optionally with cooling. The reaction is generally carried out at a temperature of from 10° to 100° C., preferably from 25° to 60° C.

After the exothermic reaction has abated, the reaction mixture is generally stirred at room temperature or, optionally, at a moderately elevated temperature within the ranges specified until analysis by thin layer chromatography or gas chromatography indicates complete conversion.

The dinitro compounds are worked up in a known manner. The dinitro compounds are often poorly soluble in the solvent used, so that the major quantity precipitates on cooling of the reaction mixture to room temperature and may be isolated by simple filtration. Another method of working up the dinitro compounds is to stir the reaction mixture into water and to recover the reaction product precipitated in the usual way by filtration. By contrast, oily reaction products are best worked up by extraction in a known manner using, for example, toluene, methylene chloride, chlorobenzene, dichlorobenzene, 1,2-dichloroethane, trichloroethylene etc. as extractant for the reaction mixture mixed with water. Another possible, but less preferred method would be to introduce the reaction mixture accumulating in nitration stage (a) directly into hydrogenation stage (b) without intermediate isolation, optionally after neutralization of the excess alkali hydroxide.

In hydrogenation stage (b) of the process of the present invention, the dinitro compounds obtained in stage (a) are converted into the corresponding diamines in a known manner by reduction with nascent hydrogen or with hydrogen catalytically activated, for example with Raney nickel or palladium on carbon. Hydrogenation generally takes place in the presence of an inert solvent of the type mentioned above (preferably dimethylformamide) or in another solvent, such as for example methanol, ethanol or isopropanol, at 20° to 120° C. and under a pressure of from 20 to 80 bar. The "solvents" are primarily suspending agents for the dinitro compounds, in which the diamines dissolve after their formation. The diamines are recovered as distillation residue during removal of the solvent by distillation.

The diamines accumulating in stage (b) of the process of the present invention are then reacted with phosgene in stage (c) to form the corresponding diisocyanates. Both the free amines and also adducts thereof with hydrogen chloride or carbon dioxide may be used. The phosgenation is generally carried out in chlorobenzene or dichlorobenzene, a reaction medium which is a suspending agent or solvent for the free amines (depending upon their constitution) and generally a solvent for the diisocyanates. The phosgenation is otherwise carried out by known methods such as those described in DE-OS No. 3,442,689, in Liebigs Annalen der Chemie, Vol. 562, 1949, pages 75 to 109; in Ullmanns Encyclopadie der technischen Chemie, Vol. 14, 4th Edition, 1977, pp. 350 to 354 and in Houben-Weyl, Methoden der organischen Chemie, Vol. E 4, 4th Edition, 1983, pp. 741 to 753.

As mentiond above, it is possible by the process of the present invention to produce both known diisocyanates, for example of the type described in DE-OS No. 3,442,689, and also new diisocyanates in which the alkylene bridge is branched. Where the diisocyanates are to be used for the production of polyurethane plastics, particularly solid or cellular polyurethane elastomers, the diisocyanates with the branched alkylene bridge of the present invention are reacted with the known reactants instead of the diisocyanates hitherto used for this purpose and disclosed for example in the literature references already cited and also in "Kunststoff-Handbuch", Vol. VIII, "Polyurethane" by Vieweg and Hochtlen, Carl-Hanser-Verlag Munich (1966), especially pages 206–297.

Thus, the production of polyurethane elastomers using a diisocyanate of the present invention may be carried out for example by reaction of the diisocyanate with (a) difunctional or trifunctional polyhydroxyl compounds having a molecular weight in the range of from 400 to 10,000, preferably from 800 to 3000, preferably the corresponding polyhydroxypolyesters or polyhydroxypolyethers, (b) chain extending agents having a molecular weight of from 60 to 399, i.e. with compounds having a functionality of 2 in the context of the isocyanate addition reaction and containing alcoholic hydroxyl groups or primary or secondary amino groups, optionally in the presence of (c) other auxiliaries and additives known to those skilled in the chemistry of polyurethane elastomers.

The polyisocyanate addition reaction may be carried out by the known prepolymer process in which the diisocyanate is reacted with a polyhydroxyl compound (a) at an equivalent ratio of isocyanate groups to isocyanate-reactive groups of greater than 1.3:1 and subsequent reaction of the NCO prepolymer thus obtained with a chain extending agent. The polyisocyanate addition process may also be carried out in a single stage by reaction of the diisocyanate with a mixture of a polyhydroxyl compound (a) and chain extending agent. In both variants, the equivalent ratio of isocyanate groups to the total quantity of isocyanate-reactive groups is generally from 0.8:1 to 1.3:1 and preferably from 0.95:1 to 1.1:1. The temperatures at which these reactions are carried out are generally in the range from 60° to 180° C., preferably from 80 to 150° C. The reactions may be carried out in the presence or even in the absence of suitable inert solvents.

The polyurethane plastics, particularly polyurethane elastomers, produced with the diisocyanates of the present invention may be solid or cellular products. The production of both types of polyurethane elastomers may be carried out by known methods of the type described, for example, in the last literature reference cited above. For example, cellular polyurethane elastomers may be produced using water alone or with another material known to be useful as a chain extending agent.

Some of the plastics, particularly elastomers, produced with the diisocyanates of the present invention show excellent mechanical and thermal properties. Accordingly, they are eminently suitable for spring and damping elements, buffers, wheel coverings, seals, shoe soles and similar applications where the material is exposed to severe mechanical and thermal stressing.

In addition, the diamines accumulating as intermediate products in the hydrogenation stage (b) of the process of the present invention are not only suitable as starting products for the diisocyanates, they are also excellent crosslinking agents or chain extending agents for precursors of plastics, for example for NCO prepolymers in the production of polyurethane elastomers or for epoxy resins. These diamines may be used instead of the polyamines hitherto used for such applications.

The invention is further illustrated by the following Examples in which all percentages are percentages by weight. The mean particle size of the powdered sodium hydroxide used was from 6 to 9 $\mu$m.

EXAMPLES

COMPARISON EXAMPLE (Reaction of 2,2-dimethyl-1,3-dihydroxypropane (neopentyl glycol) with 4-nitrochlorobenzene in accordance with DE-OS No. 2,634,419)

A mixture of 26 g (0.25 mol) neopentyl glycol, 86.6 g (0.55 mol) 4-nitrochlorobenzene, 60 g 50% sodium hydroxide, 200 ml chlorobenzene and 5.6 g triethylbenzylammonium chloride was stirred for 12 hours at 90° C. Analysis by gas chromatography revealed the following product distribution in the organic phase (solution in chlorobenzene):

Approx. 56% 4,4'-dichloroazoxybenzene
Approx. 33% 2,2-dimethyl-3-(4-nitrophenoxy)-propanol
Approx. 10% 4-nitrochlorobenzene
Approx. 1% 4-nitrophenol
Bis-(4-nitrophenoxy)-2,2-dimethylpropane could be detected at best in trace amounts.

Stage a) of the process of the present invention is illustrated in Examples 1 to 9 below with the aid of a few selected reactants.

EXAMPLE 1

1,3-bis-(4-nitrophenoxy)-2,2-dimethylpropane 140 g powdered sodium hydroxide were added in small portions with thorough stirring over a period of 3 hours to a solution of 104 g (1 mol) neopentyl glycol and 346.5 g (2.2 mols) 4-nitrochlorobenzene in 600 ml dimethylsulfoxide (DMSO). An internal temperature of 40°–50° C. was maintained by cooling with ice both during the addition and subsequently until the exothermic reaction abated. The reaction mixture was then stirred for 8 hours at 25° C. The product precipitated was filtered off under suction, washed first with water until neutral and then once with ethylacetate and then dried in vacuo at 90° C.

Yield: 321 g (92.8% of the theoretical)
Mp.: 165°–167° C. (pale yellow powder)

EXAMPLE 2

1,3-bis-(4-nitrophenoxy)-2,2-dimethylpropane

The procedure and reactants were the same as in Example 1, except that the reaction was carried out in 600 ml dimethylformamide (DMF) as solvent.

Yield: 242 g (69.9% of the theoretical)
Mp.: 165°–166° C. (beige powder)

EXAMPLE 3

1,3-bis-(4-nitrophenoxy)-2,2-diethylpropane 132 g (1 mol) 2,2-diethyl-1,3-dihydroxypropane, 346.5 g (2.2 mols) 4-nitrochlorobenzene and 140 g powdered sodium hydroxide were reacted in the same manner as was described in Example 1 in 600 ml DMSO.

Yield: 277 g (74.1% of the theoretical)
Mp.: 108°–109° C. (beige powder)

EXAMPLE 4

1,3-bis-(4-nitrophenoxy)-2-methyl-2-propylpropane 132 g (1 mol) 2-methyl-2-propyl-1,3-dihydroxypropane, 346.5 g (2.2 mols) 4-nitrochlorobenzene and 140 g powdered sodium hydroxide were reacted in the same manner as was described in Example 1 in 600 ml DMSO.

Yield: 310 g (82.9% of the theoretical)
Mp.: 124°–125° C. (beige powder)

EXAMPLE 5

1,3-bis-(4-nitrophenoxy)-2,2,4-trimethylpentane 146 g (1 mol) 2,2,4-trimethyl-1,3-dihydroxypentane, 346.5 g (2.2 mols) 4-nitrochlorobenzene and 140 g powdered sodium hydroxide were reacted using the same procedure described in Example 1 in 600 ml DMSO.

Yield: 265 g (68.3% of the theoretical)
Mp.: 95–96° C. (beige powder)

EXAMPLE 6

1,2-bis-(4-nitrophenoxy)-propane 76 g (1 mol) 1,2-dihydroxypropane, 346.5 g (2.2 mols) nitrochlorobenzene and 140 g powdered sodium hydroxide were reacted following the procedure described in Example 1 in 600 ml DMSO.

Yield: 213 g (67% of the theoretical)
Mp.: 98–99° C. (beige powder)

EXAMPLE 7

1,2-bis-(4-nitrophenoxy)-ethane 62 g (1 mol) ethylene glycol, 346.5 g (2.2 mols) 4-nitrochlorobenzene and 140 g powdered sodium hydroxide were reacted following the procedure described in Example 1 in 600 ml DMSO.

Yield: 266 g (87.5% of the theoretical)
Mp.: 153–154° C. (beige powder)

EXAMPLE 8

1,2-bis-(4-nitrophenoxy)-ethane 183 g (1 mol) 1-(2-hydroxyethoxy)-4-nitro-benzene, 173.3 g (1.1 mols) 4-nitrochlorobenzene and 70 g powdered sodium hydroxide were reacted following the procedure described in Example 1 in 600 ml DMSO.

Yield: 264 g (86.8% of the theoretical)

EXAMPLE 9

1,3-bis-(2-nitrophenoxy)-2,2-dimethylpropane 104 g (1 mol) neopentyl glycol, 346.5 g (2.2 mols) 2-nitrochlorobenzene and 140 g powdered sodium hydroxide were reacted following the procedure described in Example 1 in 600 ml DMSO.

Yield: 203 g (58.7% of the theoretical)
Mp.: 89–90° C. (beige powder)

The hydrogenation of some of the bis-nitrophenoxyalkanes described in Examples 1 to 9 to the corresponding bis-aminophenoxyalkanes serving as intermediate products (stage (b) of the process of the present invention) is illustrated in Examples 10 to 14.

EXAMPLE 10

1,3-bis-(2-aminophenoxy)-2,2-dimethylpropane 343 g 1,3-bis-(2-nitrophenoxy)-2,2-dimethyl-propane were hydrogenated at 60° C./50 bar in 1800 ml DMF in the presence of 53 g Raney nickel. After the uptake of hydrogen had stopped, the catalyst was filtered off and the solvent was removed in vacuo.

Yield: 283 g (quantitative) (dark oil) (GC: 98.7%)

EXAMPLE 11

1,3-bis-(4-aminophenoxy)-2,2-dimethylpropane 1949 g 1,3-bis-(4-nitrophenoxy)-2,2-dimethylpropane were hydrogenated as in Example 10 in 10 l DMF in the presence of 300 g Raney nickel. The crude product was recrystallized from ethanol/isopropanol (1:1).

Yield: 1466 g (91% of the theoretical)
Mp.: 116–117° C. (colorless crystals)

EXAMPLE 12

1,3-bis-(4-aminophenoxy)-2,2-diethylpropane 270 g 1,3-bis-(4-nitrophenoxy)-2,2-diethylpropane were hydrogenated by the same procedure as that of Example 10 in 1400 l DMF in the presence of 42 g Raney nickel. The crude product was recrystallized from isopropanol.

Yield: 160 g (70.6% of the theoretical)
Mp.: 100° C. (colorless crystals)

EXAMPLE 13

1,3-bis-(4-aminophenoxy)-2-methyl-2-propylpropane 300 g 1,3-bis-(4-nitrophenoxy)-2-methyl-2-propylpropane were hydrogenated as in Example 10 in 1500 ml DMF in the presence of 46 g Raney nickel. The crude product was recrystallized from toluene.

Yield: 203 g (80.6% of the theoretical)
Mp.: 54–55° C. (colorless crystals)

EXAMPLE 14

1,3-bis-(4-aminophenoxy)-2,2,4-trimethylpentane 250 g 1,3-bis-(4-nitrophenoxy)-2,2,4-trimethylpentane were hydrogenated as in Example 10 in 1300 ml DMF in the presence of 39 g Raney nickel.

Yield: 210 g (quantitative) (brownish oil) (GC: 99.3%)

The production of the diisocyanates of the present invention by phosgenation of the bis-amino-phenoxyalkanes described in Examples 10 to 14 (stage c) of the process of the present invention) is illustrated in Examples 15 to 19 below.

EXAMPLE 15

1,3-bis-(2-isocyanatophenoxy)-2,2-dimethylpropane 2.5 liters chlorobenzene were introduced into a 4 liter laboratory phosgenation reactor, after which approximately 400 g phosgene were incorporated by condensation. A solution of 300 g 1,3-bis-(2-amino-phenoxy)-2,2-dimethylpropane in 300 ml chlorobenzene was then added dropwise to this solution with stirring at −10 to 0° C. over a period of 1 hour during which phosgene was slowly introduced (40 to 50 g/h). After the addition, the mixture was heated for 3 hours to reflux temperature while more phosgene was introduced and then refluxed for another hour. An almost clear solution formed. Excess phosgene was blown out with nitrogen and the undissolved material was filtered off. After removal of the solvent, the residue was distilled in vacuo. The product solidified in the receiver.

Yield: 241 g (71.3% of the theoretical)
Bp.: 190–203° C./0.4 mbar; Mp.: 61–63° C.
NCO: calc.: 24.85% found: 24.4%
Hydrolyzable chlorine: 0.007%

EXAMPLE 16

1,3-bis-(4-isocyanatophenoxy)-2,2-dimethylpropane

Approximately 200 g phosgene were rapidly introduced with stirring at −10 to 0° C. into a suspension of 143 g 13-bis-(4-aminophenoxy)-2,2-dimethylpropane in 1400 ml chlorobenzene. Phosgenation was completed in the same way as described in Example 15.

Yield: 160 g (94.7% of the theoretical)
Bp.: 185–200° C./0.1 mbar; Mp.: 50° C.
NCO: calc.: 24.85%, found: 24.8%
Hydrolyzable chlorine: 0.005%

EXAMPLE 17

1,3-bis-(4-isocyanatophenoxy)-2,2-diethylpropane

Approximately 200 g phosgene were rapidly introduced with stirring at −10 to 0° C. into a suspension of 157 g 1,3-bis-(4-aminophenoxy)-2,2-diethylpropane in 1500 l chlorobenzene. Phosgenation was completed in the same way as described in Example 15.

Yield: 153 g (83.6% of the theoretical)
Bp.: 215–225° C./0.2 mbar; Mp.: 56–57° C.
NCO: calc.: 23.0%, found: 23.0%
Hydrolyzable chlorine: 0.002%

EXAMPLE 18

1,3-bis-(4-isocyanatophenoxy)-2-methyl-2-propylpropane 210 g 1,3-bis-(4-aminophenoxy)-2-methyl-2-propylpropane were phosgenated as in Example 15 in 1200 ml chlorobenzene.

Yield: 177 g (72.3% of the theoretical)
Bp.: 215–225° C./0.2 mbar (pale yellow oil)
Viscosity: 705 mPas/23° C., D (23° C.): 1.036
NCO: calc.: 23.0%; found: 23.2%
Hydrolyzable chlorine: 0.027%

EXAMPLE 19

1,3-bis-(4-isocyanatophenoxy)-2,2,4-trimethylpentane 210 g 1,3-bis-(4-aminophenoxy)-2,2,4-trimethyl-pentane were phosgenated as described in Example 15 in 1800 ml chlorobenzene.

Yield: 130 g (53.4% of the theoretical)
Bp: 215–230° C./0.2 mbar (pale yellow oil)
Viscosity: 345 mPas/23° C., D (23° C.): 1.026
NCO: calc.: 22.1%, found: 21.9%

Hydrolyzable chlorine: 0.005%

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the production of diisocyanates corresponding to the formula

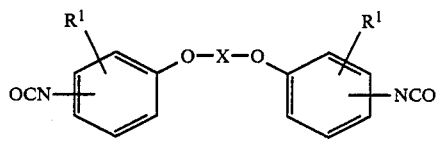

comprising
(a) reacting
  (1) a monofunctional or difunctional alcohol corresponding to the following formula I or formula II

  (I)

or

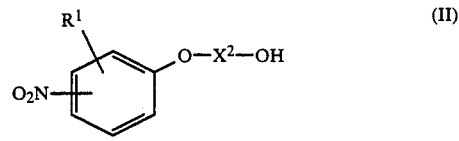  (II)

with
(2) a compound corresponding to the formula

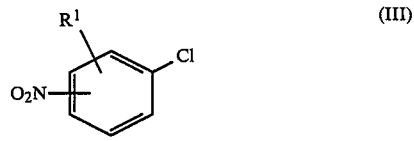  (III)

in the presence of
(3) powdered sodium hydroxide and/or potassium hydroxide in a quantity sufficient to neutralize eliminated hydrogen chloride and
(4) a strongly polar, aprotic solvent to form a dinitro compound corresponding to the formula

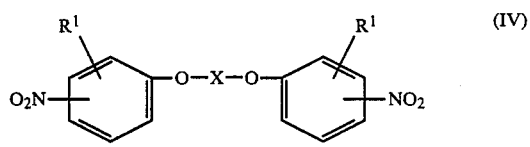  (IV)

with the radicals in each of formulae (I) through (IV) having the following meanings:
$R^1$ represents hydrogen or a methyl group
$X^1$ represents a difunctional aliphatic hydrocarbon radical containing from 2 to 31 carbon atoms
$X^2$ represents a difunctional aliphatic hydrocarbon radical containing from 2 to 9 carbon atoms which may be interrupted by ether bridges provided that at least two carbon atoms are present before such interruption and
X represents $X^1$ or $X^2$ (b) hydrogenating the dinitro compound to produce the corresponding diprimary diamine and
(c) phosgenating the diamine obtained in (b) to produce the desired isocyanate.

2. The process of claim 1 in which the alcohol of (a) (i) is a diol corresponding to the formula

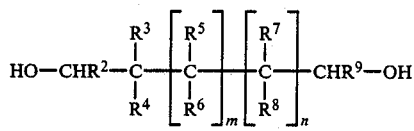
(V)

in which
R$^2$, R$^3$, R$^5$, R$^6$, R$^7$, R$^8$ and R$^9$ each represent hydrogen or a C$_1$-C$_4$ alkyl radical,
R$^4$ represents a C$_1$-C$_4$ alkyl radical and
m and n each represent 0 or 1.

3. The process of claim 2 in which R$^2$, R$^5$, R$^6$, R$^7$ and R$^9$ each represent hydrogen, R$^3$ and R$^4$ each represent a methyl group and R$^8$ represents hydrogen or a methyl group.

4. The process of claim 3 in which R$^1$ of formula III represents hydrogen and the chlorine and nitro groups of the compound represented by formula III are either ortho or para to one another.
* * * * *